United States Patent [19]

Landis et al.

[11] Patent Number: 4,948,920

[45] Date of Patent: Aug. 14, 1990

[54] PROCESS FOR THE PREPARATION OF PHENYLPYRUVIC ACID FROM BENZYL CHLORIDE

[75] Inventors: Clark R. Landis, Boulder, Colo.; Hayat Khowaja, Belleville, Ill.

[73] Assignee: The NutraSweet Company, Deerfield, Ill.

[21] Appl. No.: 328,410

[22] Filed: Mar. 24, 1989

[51] Int. Cl.$^5$ ............................................. C07C 51/04
[52] U.S. Cl. ..................................... 562/406; 560/51; 562/459
[58] Field of Search ................... 562/406, 459; 560/51

[56] References Cited

U.S. PATENT DOCUMENTS

| | | | |
|---|---|---|---|
| 4,128,572 | 12/1978 | Cassar et al. | 562/406 |
| 4,152,352 | 5/1979 | Perron | 562/406 |
| 4,351,952 | 9/1982 | Foà et al. | 562/406 |
| 4,447,644 | 5/1984 | El-Chahawi | 562/406 |
| 4,481,369 | 11/1984 | Wolfram | 562/406 |
| 4,575,561 | 11/1986 | Sawicki | 560/105 |
| 4,689,431 | 8/1987 | Tanaka et al. | 562/406 |

Primary Examiner—Werren B. Lone
Assistant Examiner—Vera C. Clarke
Attorney, Agent, or Firm—Craig M. Bell

[57] ABSTRACT

A process for producing phenylpyruvic acid by reacting benzyl chloride with carbon monoxide in the presence of a catalytic amount of a metal carbonyl compound and an inorganic base, in an acetonitrile/water solvent.

13 Claims, No Drawings

PROCESS FOR THE PREPARATION OF PHENYLPYRUVIC ACID FROM BENZYL CHLORIDE

BACKGROUND OF THE INVENTION

1. Field of the Invention

This invention relates to a process for the production of phenylpyruvic acid, an intermediate in the production of L-phenylalanine, a component of the popular dipeptide sweetener, aspartame. The process involves a carbonylation reaction wherein benzyl chloride is reacted in a solvent with carbon monoxide in the presence of a catalytic amount of a cobalt carbonyl compound and an inorganic base. The solvent is acetonitrile:water.

2. Prior Art

The prior art describes numerous processes for the production of arylpyruvic acids, including phenylpyruvic acid, by carbonylation of benzyl halide, usually carried out with catalytic amounts of a carbonyl compound.

U.S. Pat. No. 4,152,352 describes a process for producing arylpyruvic acids by reacting an arylmethylhalide with carbon monoxide, in the presence of a carbonyl catalyst, an alkaline earth metal hydroxide, oxide or carbonate in a solvent which is alcohol, water, or an alcohol/water mixture.

U.S. Pat. No. 4,351,952 describes a process for producing phenylpyruvic acids by reacting a benzyl halide with carbon monoxide in the presence of a carbonyl catalyst and an inorganic base in a solvent which is a water-miscible ether.

U.S. Pat. No. 4,447,644 describes a process for producing arylpyruvic acids by reacting an arylmethylhalide with carbon monoxide in the presence of a carbonyl catalyst and an alkali metal hydroxide in a solvent which is a branched chain alcohol.

U.S. Pat. Nos. 4,481,368 and 4,481,369 describe a stoichiometric process for producing α-keto-carboxylic acids by reacting an acyl halide with an alkali metal cobaltate complex (obtained by reducing a metal carbonyl) to form an intermediate acylcobalt complex, reacting the cobalt complex with carbon monoxide at elevated temperature and pressure in a solvent medium and thereafter acidifying the reaction mixture. Suitable solvents are described as solvents which are inert under the reaction conditions; suitable dipolar aprotic solvents include N,N-dimethylacetonitrile and acetonitrile. Other suitable solvents include low boiling hydrocarbons and halogenated hydrocarbons.

Some of the above-described processes for carbonylation of benzyl halides suffer from the disadvantage of requiring high pressure or temperature or producing significant amounts of undesirable by-products, e.g., phenylacetic acid. Reactions involving acyl halides require the use of expensive starting materials and stoichiometric consumption of metal carbonyls. There is a need for an economical process for the catalytic production of phenylpyruvic acid on a commercial scale.

3. Summary of the Invention

The present invention is directed to an improved process for producing phenylpyruvic acid from benzyl chloride. The process involves reacting benzyl chloride with carbon monoxide (CO) in the presence of a catalytic amount of a metal carbonyl compound and an inorganic base in a liquid solvent medium and obtaining therefrom phenylpyruvic acid. The improvement comprises the use of acetonitrile:water as a solvent.

4. Detailed Description

The carbonylation process of the present invention to produce phenylpyruvic acid can be carried out in a closed autoclave reactor of a desired capacity.

The autoclave is charged with an inorganic base, benzyl chloride, a metal carbonyl catalyst and acetonitrile:water as a solvent. The order of charging the reactants is not critical to the process. It is convenient to first charge the inorganic base, and add the benzyl chloride, metal carbonyl catalyst, and solvent under a CO atmosphere, or alternatively,, the reactants can be charged simultaneously under a CO atmosphere.

Prior to, or after charging of the reactants, CO is introduced into the autoclave. The autoclave temperature can be at room temperature and thereafter increased as described hereinafter. The benzyl chloride, CO and inorganic base react to form a salt of phenylpyruvic acid. The salt can be converted to phenylpyruvic acid by conventional acidification techniques, and the desired phenylpyruvic acid obtained therefrom.

The carbonylation process can be carried out at any temperature wherein the benzyl chloride, CO and inorganic base, in the presence of a metal carbonyl catalyst, react to form a salt of phenylpyruvic acid. The process can be carried out at a temperature range of from about 10° to 100° C. At a lower temperature within this range, the reaction proceeds at a slower rate. A preferred temperature range is from about 40° to 80° C.

In a similar manner, the CO pressure should be sufficient wherein the benzyl chloride, CO and inorganic base, in the presence of a metal carbonyl catalyst, react to form a salt of phenylpyruvic acid. The CO can be present in a pressure range of from about 1 bar Absolute to about 30 bars Absolute. A pressure greater than 30 bars can be used with satisfactory results, but for economic reasons, a lower pressure is preferred.

The solvent used is acetonitrile:water in a volume:-volume ratio of from 1:10 to 10:1 acetonitrile:water. A preferred ratio is from 1:5 to 5:1; a most preferred ratio is from 1:1 to 2:1. The amount of water present effects the reaction rate and selectivity to a salt of phenylpyruvic acid. Optimization of the acetonitrile:water ratio at the desired reaction temperature can be easily carried out by one skilled in the art by conducting a carbonylation reaction at a selected acetonitrile:water ratio, as taught herein, and by determining the amount of phenylpyruvic acid salt formed. A series of reactions can be carried out and the optimum acetonitrile:water ratio selected.

The presence of sufficient water helps to provide phase separation, described hereinafter. Phase separation is advantageous if it is desired to recover and recycle the catalyst utilized in the reaction.

In the process described herein, it is preferred to use metal carbonyl compounds as carbonylation catalysts, e.g., iron pentacarbonyl, nickel tetracarbonyl and dicobalt octacarbonyl. Dicobalt octacarbonyl salts are particularly suited and include calcium, potassium or sodium salts. Dicobalt octacarbonyl, hydridocobalt tetracarbonyl and cobalt tetracarbonylate salts are preferred catalysts. The molar ratio of cobalt catalyst required based on the amount of benzyl chloride present, is from about 1:2 to 1:1,000. A molar ratio between 1:10 and 1:200 is preferred.

The carbonylation reaction requires the presence of an inorganic base. A suitable alkali metal hydroxide can be NaOH, KOH or LiOH. A suitable alkaline earth metal hydroxide can be $Ca(OH)_2$, $Mg(OH)_2$ or $Ba(OH)_2$. For economic reasons, a preferred inorganic base is $Ca(OH)_2$. The amount of inorganic base for the carbonylation reaction, based on the amount of benzyl chloride present, is from about 1:1.5 to 1:10, on a molar ratio basis. A preferred range of alkaline earth metal hydroxide is from 1:1.5 to 1:3. A larger excess can be used, but requires greater amounts of acid for neutralization at the completion of reaction.

The present process has been found to be an economically feasible process for a number of reasons. First, because the reaction can be carried out at low pressure and temperature, the reaction vessels can be low-temperature, and low-pressure equipment. Further, as described in detail below, the use of acetonitrile:water as a solvent provides advantageous phase separation.

When $Ca(OH)_2$ is used, at the completion of the carbonylation reaction, there are four phases present. One phase is a solid phase containing calcium phenylpyruvate and unreacted $Ca(OH)_2$. A second phase is an organic phase of acetonitrile containing catalytically active metal carbonyl, a small amount of dissolved calcium phenylpyruvate and organic impurities, e.g. bibenzyl alcohol and benzyl alcohol. A third phase is an aqueous phase which is, in effect, "salted out" from the organic phase and contains chloride salts and the calcium salt of phenylacetate. A fourth phase is a gaseous phase of CO.

The desired phenylpyruvic acid can be easily obtained from the solid calcium phenylpyruvate present by acidification. The organic phase can be separated by conventional liquid separation techniques, for example, decanting or filtration, and the cobalt catalyst recovered and recycled.

The following Examples are provided to illustrate and better define the present invention. They are presented for illustrative purposes only and since minor variations in methodologies or materials will become evident to one skilled in the art, they are not to be construed as limiting the spirit and scope of the claims.

EXAMPLE 1

A 300 ml autoclave with stirring equipment was charged with 7.50 g (101 mmoles) calcium hydroxide. The autoclave was then pressurized to 80 psig with argon and vented; this procedure was repeated three times to purge the air from the autoclave. The autoclave was then charged with a reaction mixture which comprised 75 mls of water, 100 mls of acetonitrile (1.3:1 volume:volume), 0.33 g (0.96 mmoles) of dicobaltoctacarbonyl and 6.33 g (50 mmoles) benzyl chloride. The autoclave was charged with CO by introducing CO at a pressure of about 19 bars Absolute, and the reaction mixture stirred at 1200 rpm, while warming the mixture from room temperature to about 75° C. The autoclave pressure rose to about 20.4 bars Absolute and was maintained at that pressure by introducing CO from a CO reservoir via a regulator. CO gas uptake, as measured by a decrease in the CO reservoir pressure, continued for two and one-half hours.

The contents of the autoclave, comprising the solid phase referred to hereinbefore, were removed and filtered under an inert (argon or nitrogen) atmosphere, and a white solid of calcium phenylpyruvate and unreacted $Ca(OH)_2$ was obtained. The white solid then was washed twice with 30 ml portions of water followed by two washings with ethanol and the washings discarded. The solid was placed in an Erlenmeyer flask and the calcium phenylpyruvate was converted to phenylpyruvic acid by slowly adding with stirring 50–60 ml of concentrated HCl and 80–100 ml of diethyl ether. After a period of fifteen to twenty minutes, all the solids dissolved and a clear blue aqueous and a light yellow ether phase appeared. The ether phase was separated from the aqueous phase and the aqueous phase extracted four times with 100 ml portions of diethyl ether. The ether extracts were combined and dried over magnesium sulfate (anhydrous) for thirty minutes, the magnesium sulfate removed by filtration, and the diethyl ether solvent removed under reduced pressure at 25° C. A pale yellow solid (6.55g) containing 93% by weight phenylpyruvic acid (37 mmoles or 74% yield based on the starting weight of benzyl chloride) was obtained. No phenylacetic acid was detected in the phenylpyruvic acid obtained.

The filtrate obtained from filtering the solid phase of the autoclave comprised an organic phase of acetonitrile and an inorganic aqueous phase.

The acetonitrile phase was examined as follows. The solvent was removed under reduced pressure at 40° C., and an oily green solid obtained. The green solid was treated with 50 ml concentrated HCl and extracted four times with 60 ml portions of diethyl ether. The yellow diethyl ether layer was concentrated to dryness and yielded an oily yellow solid (1.50 g) containing phenylacetic acid (0.84 g, 6.2 mmoles, analyzed by gaseous liquid phase chromatography) and small amounts (less than two mmoles) of organic compounds containing a benzyl fragment.

Analysis of the reaction mixture indicated that the water phase contained 0.88 g (6.5 mmoles) of phenylacetic acid.

EXAMPLE 2

A 300 ml autoclave with stirring equipment was charged with 7.50 g (101 mmoles) calcium hydroxide. The autoclave was then pressurized to 80 psig with argon and vented; this procedure was repeated three times. The autoclave was then charged with a reaction mixture which comprised 75 mls of water, 100 mls of acetonitrile, $CH_3CH:H_2O$ (1.3:1 volume:volume), 0.678 g (1.92 mmoles) of dicobaltoctacarbonyl and 6.33 g (50 mmoles) benzyl chloride. The autoclave atmosphere was charged with CO at a pressure of about 2 bars Absolute, and the reaction mixture stirred at 1200 rpm, while warming the mixture from room temperature to about 75° C. The autoclave pressure was maintained at about 3.3 bars Absolute pressure by introducing CO from a CO reservoir via a regulator. CO gas uptake, as measured by a decrease in the CO reservoir pressure, continued for four and one-half hours.

The contents of the autoclave were removed and the procedure described in Example 1 followed. A pale yellow solid (5.1 g) by weight phenylpyruvic acid or 62% yield based on benzyl chloride charge was obtained.

EXAMPLE 3

The procedure of Example 2 was repeated, using the amounts of reactants indicated therein, at a CO pressure of 3.3 bars, for a reaction time of four and two-third hours. A 44% yield of phenylpyruvic acid was obtained.

EXAMPLE 4

The procedure of Example 2 was repeated, except that 0.33 g (0.93 mmoles) of dicobaltoctacarbonyl was present in the reaction mixture.

The autoclave pressure was maintained at about 1.4 bars Absolute pressure. A 50 percent yield of phenylpyruvic acid was obtained.

In a similar manner, other examples of the present invention were carried out, using varying conditions of reaction and different reactants. The amounts of reactants, conditions and yields of phenylpyruvic acid are given in the following table.

TABLE 1

| Example No. | $\Phi CH_2Cl$ mmoles | $Ca(OH)_2$ mmoles | $Co_2(CO)_8$ mmoles | $H_2O$ mls | $CH_3CN$ mls | $Ac:H_2O$ | Temp. °C. | CO (Bars) | Yield of PPA (%) |
|---|---|---|---|---|---|---|---|---|---|
| 5  | 50  | 101 | 0.96 | 125 | 50  | 1:2.5 | 60 | 20   | 47   |
| 6  | 50  | 101 | 0.96 | 100 | 75  | 1:1.3 | 60 | 20   | 46   |
| 7  | 50  | 101 | 0.96 | 100 | 75  | 1:1.3 | 60 | 60   | 42   |
| 8  | 50  | 101 | 0.96 | 100 | 75  | 1:1.3 | 60 | 3.3  | 38   |
| 9  | 50  | 101 | 1.97 | 100 | 75  | 1:1.3 | 60 | 3.3  | 44   |
| 10 | 50  | 101 | 0.96 | 75  | 100 | 1.3:1 | 60 | 20   | 66   |
| 11 | 50  | 101 | 1.97 | 75  | 100 | 1.3:1 | 60 | 3.3  | 63   |
| 12 | 50  | 101 | 0.96 | 75  | 100 | 1.3:1 | 45 | 20   | 54   |
| 13 | 50  | 101 | 0.96 | 75  | 100 | 1.3:1 | 75 | 20   | 74   |
| 14 | 50  | 101 | 0.97 | 75  | 100 | 1.3:1 | 75 | 8.3  | 66   |
| 15 | 50  | 101 | 0.97 | 75  | 100 | 1.3:1 | 85 | 20   | 67   |
| 16 | 100 | 202 | 0.97 | 75  | 100 | 1.3:1 | 75 | 20   | 66.3 |
| 17 | 50  | 101 | 0.97 | 75  | 100 | 1.3:1 | 95 | 20   | 39   |
| 18 | 50  | 51  | 0.97 | 75  | 100 | 1.3:1 | 75 | 20   | 14   |
| 19 | 50  | 202 | 3.8  | 75  | 100 | 1.3:1 | 75 | 20   | 61   |
| 20 | 50  | 202 | 3.8  | 75  | 100 | 1.3:1 | 60 | 20   | 68   |
| 21 | 50  | 202 | 3.8  | 75  | 100 | 1.3:1 | 60 | 100  | 40   |
| 22 | 50  | 100 | 3.8  | 75  | 100 | 1.3:1 | 75 | 100  | 54   |
| 23 | 50  | 101 | 0.96 | 60  | 115 | 1.9:1 | 60 | 20   | 70   |
| 24 | 50  | 100 | 3.8  | 60  | 115 | 1.9:1 | 60 | 8.3  | 70   |
| 25 | 50  | 101 | 0.96 | 50  | 125 | 2.5:1 | 60 | 20   | 59   |
| 26 | 50  | 101 | 0.97 | 50  | 125 | 2.5:1 | 75 | 20   | 63   |
| 27 | 50  | 101 | 0.96 | 25  | 150 | 6:1   | 60 | 20   | 34   |

COMPARATIVE PROCEDURE

For comparative purposes, the production of phenylpyruvic acid by the above-described reaction involving carbonylation of benzyl chloride was attempted utilizing propionitrile and N,N-dimethyl-acetonitrile, respectively, as a solvent. The experimental results obtained are described below.

In each of the comparative procedure reactions, the procedure described in Example 2 was followed. The following amounts of reactants were used:

| | |
|---|---|
| Temperature: | 75° C. |
| Benzyl chloride: | 6.33 g (50 mmoles) |
| $Ca(OH)_2$: | 7.5 g (101 mmoles) |
| Dicobaltoctacarbonyl: | 0.33 g (0.96 mmoles) |

The solvent:water ratio used is indicated below:

| Solvent | Solvent:Water (Volume:Volume) | Yield of Phenyl-pyruvic Acid |
|---|---|---|
| A. Propionitrile | 100:75 | 8% |
| B. N,N-Dimethylacetamide | 100:75 | 2% |

The above summarized experimental results indicate that propionitrile and N,N-dimethylacetonitrile solvents, which are related in structure to acetonitrile, produced low yields of phenylpyruvic acid, 8 percent and 2 percent, respectively.

What we claim is:

1. In a process for the production of phenylpyruvic acid which comprises the carbonylation of benzyl chloride with carbon monoxide in a liquid solvent, in the presence of a catalytic amount of a metal carbonyl catalyst and an inorganic base to produce a salt of phenylpyruvic acid, acidifying said salt and obtaining therefrom phenylpyruvic acid, the improvement wherein the liquid solvent is acetonitrile:water.

2. A process as claimed in claim 1 wherein the inorganic base is an alkali metal hydroxide or alkaline earth metal hydroxide.

3. A process as claimed in claim 2 wherein the inorganic base is $Ca(OH)_2$.

4. A process as claimed in claim 2 wherein the metal carbonyl catalyst is tetracarbonyl cobalt.

5. A process as claimed in claim 4 wherein the metal carbonyl catalyst is dicobaltoctacarbonyl.

6. A process as claimed in claim 1 wherein the acetonitrile:water is present in a volume:volume ratio of from 1:10 to 10:1.

7. A process as claimed in claim 1 wherein the acetonitrile:water is present in a volume:volume ratio of from 1:1 to 2:1.

8. A process as claimed in claim 1 wherein the CO pressure is from about 1 to 50 bars Absolute.

9. A process for producing phenylpyruvic acid by reacting benzyl chloride with carbon monoxide in the presence of a catalytic amount of a metal carbonyl catalyst and an inorganic base and a carbon monoxide pressure of from about 1 to 50 bars Absolute, in a liquid solvent medium which is acetonitrile:water in a volume:volume ratio of from 10:1 to 1:10, to produce a salt of phenylpyruvic acid, acidifying said salt and obtaining therefrom phenylpyruvic acid.

10. A process as claimed in claim 9 wherein the acetonitrile:water ratio is from 1:2 to 2:1.

11. A process as claimed in claim 9 wherein the metal carbonyl catalyst is tetracarbonyl cobalt.

12. A process as claimed in claim 9 wherein the metal carbonyl catalyst is dicobaltoctacarbonyl.

13. A process as claimed in claim 9 wherein the inorganic base is $Ca(OH)_2$.

* * * * *